United States Patent [19]

Law et al.

[11] Patent Number: 5,656,500

[45] Date of Patent: Aug. 12, 1997

[54] LUMINESCENT CONJUGATES FOR USE IN LUMINESCENT ASSAYS

[75] Inventors: Say-Jong Law, Westwood; Uri Piran, Sharon, both of Mass.

[73] Assignee: Chiron Diagnostics Corporation, Walpole, Mass.

[21] Appl. No.: 440,427

[22] Filed: May 12, 1995

Related U.S. Application Data

[60] Continuation of Ser. No. 325,845, Oct. 19, 1994, Pat. No. 5,595,875, which is a division of Ser. No. 32,321, Mar. 17, 1993, Pat. No. 5,449,556, which is a division of Ser. No. 826,186, Jan. 22, 1992, Pat. No. 5,227,489, which is a continuation of Ser. No. 226,639, Aug. 1, 1988, abandoned.

[51] Int. Cl.[6] .................................................. G01N 33/533
[52] U.S. Cl. ................... 436/56; 428/402.2; 428/402.21; 428/402.22
[58] Field of Search ..................... 428/402.2, 402.21, 428/402.22; 536/26.6; 436/56

[56] References Cited

U.S. PATENT DOCUMENTS

| | | | |
|---|---|---|---|
| 3,352,791 | 11/1967 | Sheehan et al. | 252/188.3 |
| 3,689,391 | 9/1972 | Ullman | 204/159 |
| 4,098,876 | 7/1978 | Piasio et al. | 424/1 |
| 4,193,983 | 3/1980 | Ullman et al. | 424/12 |
| 4,244,940 | 1/1981 | Jeong et al. | 424/1 |
| 4,656,129 | 4/1987 | Wagner | 435/7 |
| 4,695,554 | 9/1987 | O'Connell et al. | 436/528 |
| 4,704,355 | 11/1987 | Bernstein | 435/6 |
| 4,745,181 | 5/1988 | Law et al. | 530/387 |
| 4,918,192 | 4/1990 | Law et al. | 546/104 |
| 4,933,121 | 6/1990 | Law et al. | 264/4.3 |
| 4,946,958 | 8/1990 | Campbell et al. | 546/104 |
| 4,950,613 | 8/1990 | Arnold et al. | 436/546 |
| 4,978,614 | 12/1990 | Bronstein | 435/21 |
| 5,004,565 | 4/1991 | Schaap | 252/700 |
| 5,094,785 | 3/1992 | Law et al. | 264/4.3 |
| 5,110,932 | 5/1992 | Law et al. | 546/102 |
| 5,281,712 | 1/1994 | McCapra et al. | 546/104 |

FOREIGN PATENT DOCUMENTS

| | | | |
|---|---|---|---|
| 0144084 | 6/1985 | European Pat. Off. | G01N 33/531 |
| 0216553 | 4/1987 | European Pat. Off. | 546/102 |
| 0257541 | 8/1987 | European Pat. Off. | C07D 219/04 |
| 0 322 926 | 12/1988 | European Pat. Off. | G01N 33/53 |
| 0322926 | 7/1989 | European Pat. Off. | G01N 33/53 |
| 0324202 | 7/1989 | European Pat. Off. | 546/102 |
| 0330050 | 8/1989 | European Pat. Off. | 546/104 |
| 0361817 | 4/1990 | European Pat. Off. | 546/102 |
| 1461877 | 1/1977 | United Kingdom | 546/102 |

OTHER PUBLICATIONS

Allen et al., 247 J. Biol Chem 7695 (1972).
Anderson et al., B33 Acta Chemica Scandinavia 695 (1979).
Applied Biosystems, Inc., Foster City, CA, User Manual for DNA/RNA Synthesizer, (1990), iii–vii, 6–1 to 6–21.
Applied Biosystems, Inc., Peptide Synthesizer User's Manual (1988), pp. 0–4 to 0–11, 6–5 to 6–18.
Clontech Laboratories, Inc., Palo Alto, CA, User Manual on DNA Modification Reagents for Use in Automated DNA Synthesis, p. 2–3.
Hammond et al., 6 J. Biolum and Chemilum., 35–43 (1991).
Hendrickson et al., Organic Chemistry, 3d. ed., McGraw Hill, NY (1970), p. 71.
Kricka, L. and Carter T., Clinical and Biochemical Luminescence, pp. 153–178 (Marcel Dekker, Inc., NY. and Basel, 1982).
March, Advanced Organic Chemistry, 3d. ed., John Wiley & Sons, NY (1985), p. 304–310, 587.
Martinet et al., Bull Soc Chim Fr., vol 45 pp. 101–109 (1929).
Mayer et al., "Hydrophilic Acridinium–9–Carboxylic Acid Derivatives Used as Labels in Luminescent Assays" in Stanley et al. Eds., p. 99 (1991, Wiley, Chichester).
Meek et al., 11 J. Chem & Eng Data, vol 14, p. 388–391 (1969).
Miller et al., 25 Ann Clin Biochem 27–34 (1988).
Patel et al., 97 CA 85407p (1982).
Richardson et al., 31/10 Clin Chem 1664–8 (1985).
Weeks et al., 29 Clin Chem 1474 (1983).

*Primary Examiner*—Scott W. Houtteman
*Attorney, Agent, or Firm*—Arthur S. Morgenstern; Maurice M. Klee; Robert P. Blackburn

[57] ABSTRACT

Vesicular luminescent conjugates comprising liposomes coupled to molecules with biological activity, such as antigens, antibodies, and nucleic acids, for use in luminescent assays, are described herein. These conjugates encapsulate hydrophilic polysubstituted aryl acridinium esters and are useful as chemiluminescent tracers in immunoassays and other binding assays.

5 Claims, 5 Drawing Sheets

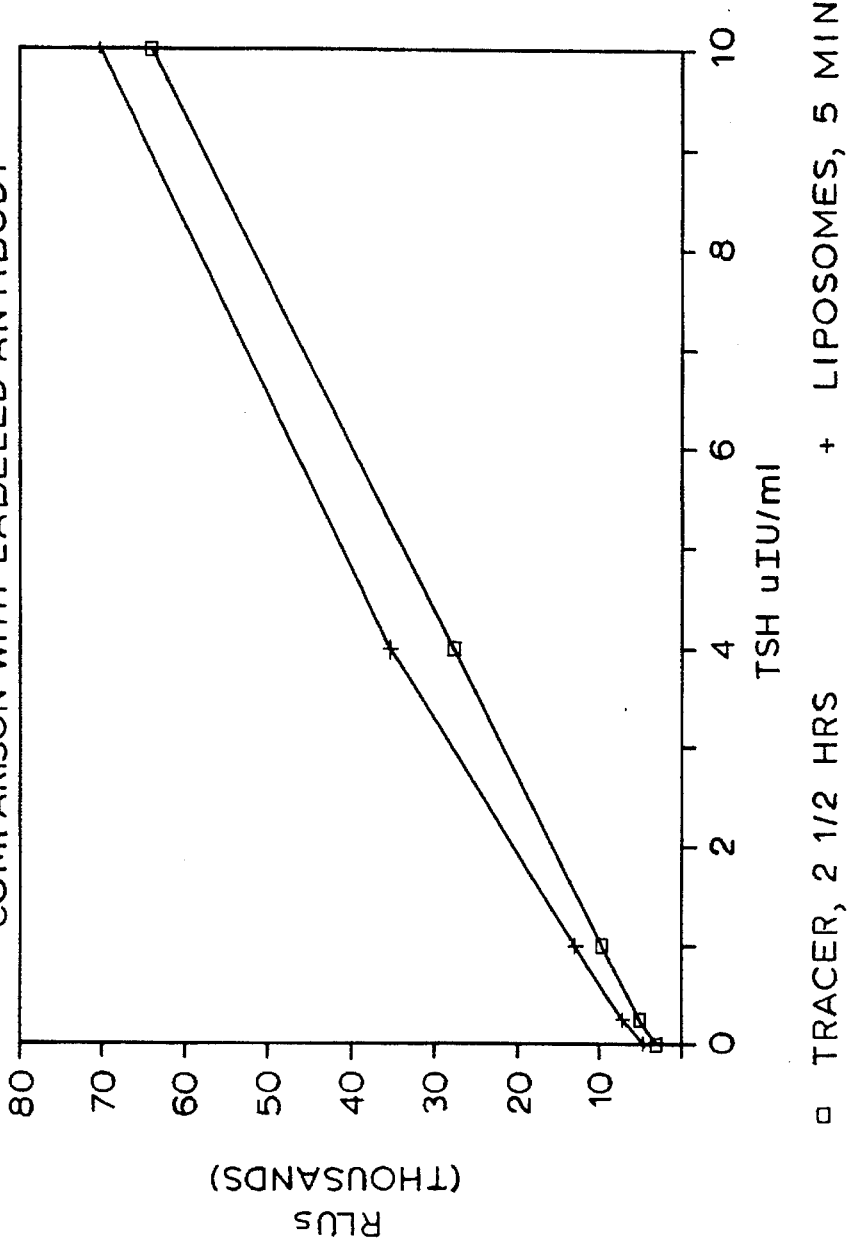

LUMINESCENT CONJUGATES FOR USE IN LUMINESCENT ASSAYS

This application is a continuation of 08/325,845, filed Oct. 19, 1994, now U.S. Pat. No. 5,595,875, which is a division of application Ser. No. 08/032,231, filed Mar. 17, 1993, now U.S. Pat. No. 5,449,556, which is a division of Ser. No. 07/826,186, filed Jan. 22, 1992, now U.S. Pat. No. 5,227,489, which is a continuation of Ser. No. 07/226,639, filed Aug. 1, 1988, now abandoned.

FIELD OF THE INVENTION

The present invention relates to a novel method for the detection of an analyte in a fluid sample. More particularly, the present invention relates to a method for the detection of an analyte in a fluid sample using acridinium esters encapsulated within the walls of liposomes (lumisomes). This invention also relates to novel acridinium esters useful as chemiluminescent markers which can be encapsulated within liposome vesicles without significant leakage of the esters from the vesicles.

BACKGROUND OF THE INVENTION

The use of liposomes as carriers of marker molecules for nonisotopic immunoassays is known. See, e.g., U.S. Pats. Nos. 4,704,355; 4,695,554; 4,656,129 and 4,193,983. An important advantage of using liposomes in immunoassays is the ability of liposomes to carry a large number of marker molecules per liposome vesicle, and thereby provide an amplified signal to immunoassays. Immunoassays utilizing liposomes with encapsulated macromolecular markers such as enzymes or small organic marker molecules such as fluorescent or absorbing dyes, spin-labels, metal chelators, and enzyme activators or inhibitors, have been described. See, e.g., Kricka, L. and Carter T., *Clinical and Biochemical Luminescence*, pp. 153–178 (Marcel Dekker, Inc., New York and Basel, 1982).

Prior to the present invention, chemiluminescent markers such as the acridinium esters described in Ann. Clin. Biochem. 25, p. 27 (1988), Clin. Chem. 31, p. 664 (1985), European Patent Application No. EP 82,636, and U.S. Pat. No. 4,745,181, have only been used as labels for immunoassays by conjugating them directly to biological molecules, such as antigens or antibodies. The lipophilic nature of the prior art acridinium esters and other chemiluminescent compounds render them unsuitable for encapsulation within liposomes because of their rapid leakage through the liposome wall. Additionally, the limited water solubility of prior art acridinium esters and other chemiluminescent compounds only allow the encapsulation of a few marker molecules per liposome vesicle, resulting in relatively low signal amplification.

Accordingly, it is the purpose of the present invention to provide a novel method for detecting an analyte using acridinium esters. It is also a purpose of the present invention to provide novel hydrophilic acridinium esters useful for encapsulation within liposomes for use as chemiluminescent markers.

BRIEF DESCRIPTION OF THE DRAWINGS

FIG. 5 is a comparison of two standard curves for a TSH Assay, the top curve representing a TSH assay using lumisomes of this invention and shortened incubation times and the bottom curve representing a TSH assay using antibody directly labelled with acridinium ester and normal incubation times.

DESCRIPTION OF THE INVENTION

Figure 1:
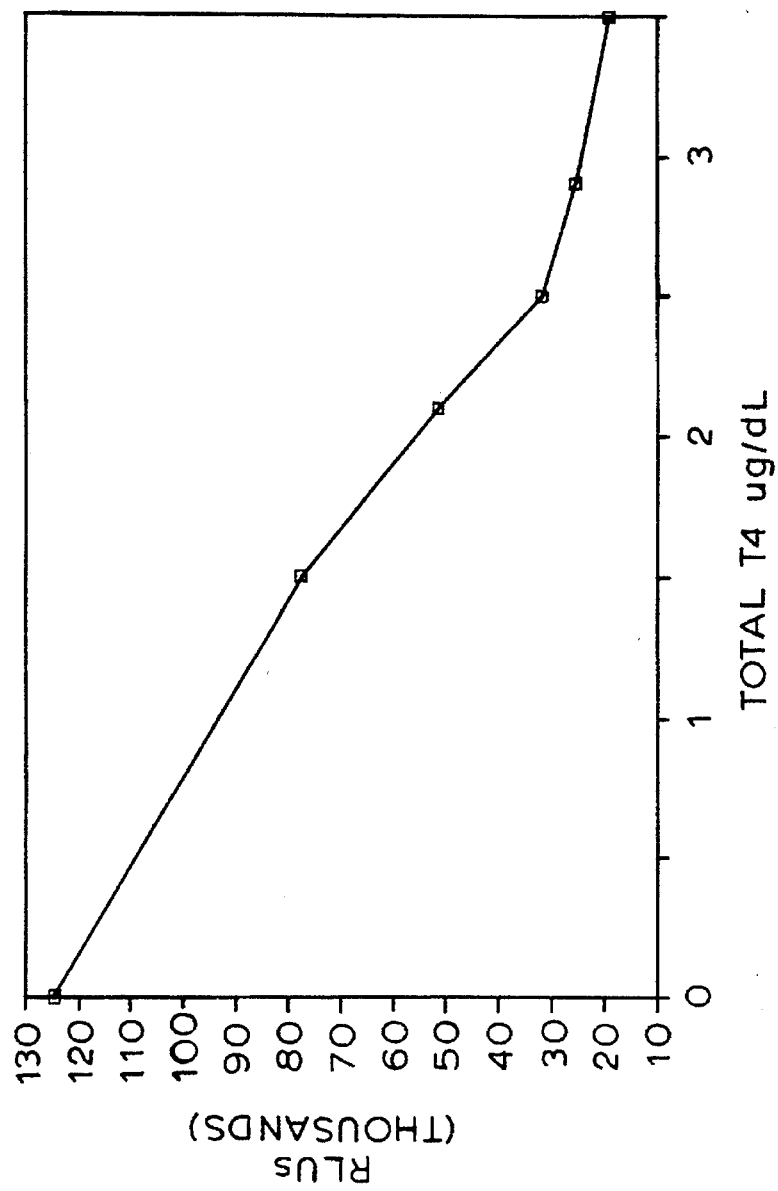
FIG. 1 is a standard curve for a Total $T_4$ Assay using lumisomes of this invention.

The following terms as used in the specification and claims shall have the following meanings:

Analyte—the compound or composition to be measured which can be a ligand that is mono- or polyepitopic, antigenic, or haptenic. The analyte can be a piece of DNA or RNA.

Antigen—any substance capable of provoking an immune response in vertebrates, particularly with the production of specific antibodies.

Hapten—an incomplete antigen, incapable by itself to provoke an immune response but when suitably attached to another molecule becomes capable of producing antibodies which will specifically recognize the hapten.

Epitope—a specific chemical and spatial configuration which is specifically recognized by an antibody.

Ligand—any compound for which a receptor naturally exists or can be prepared.

Ligand analog—a modified ligand which can compete with the analogous ligand for a receptor, the modification providing means to join a modified ligand to another molecule.

Receptor—any compound capable of recognizing a particular spatial and polar organization of a molecule, i.e., epitopic site. Illustrative receptors include antibodies, enzymes, antibody fragments, such as Fab fragments, DNA or RNA fragments, lectins, complement components, conglutin, rheumatoid factors, hormones, avidin, staphylococcal protein A, and the like.

Antiligand—a receptor for a ligand.

DNA probe—piece of DNA that recognizes specific DNA or RNA sequences by hydridizing to complementary DNA or RNA.

RNA probe—piece of RNA that recognizes specific DNA or RNA sequences by hydridizing to complementary DNA or RNA.

Liposomes—single or multicompartmented bodies obtained when lipids, particularily lipid mixtures, are dispersed in aqueous suspension. The walls or membranes are composed of a continuous lipid bilayer.

Lumisomes—liposomes comprising an encapsulated acridinium ester.

The acridinium esters useful in the method of the present invention can be any acridinium ester which can be encapsulated within a liposome and which can generate a chemiluminescent signal. Preferred acridinium esters include acridinium esters of the following formula:

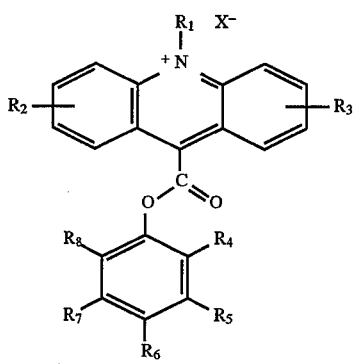

wherein $R_1$ is alkyl, alkenyl, alkynyl, aryl, or aralkyl, containing from 0 to 20 heteroatoms, preferably nitrogen, oxygen, phosphorous or sulfur;

$R_2$, $R_3$, $R_5$, and $R_7$ are hydrogen, amino, alkoxyl, hydroxyl, —COOH, halide, nitro, —CN, —SO$_3$H, —NHCR, —CR, —COR, —CNHR, or —SCN,
            ‖     ‖    ‖    ‖
            O     O    O    O wherein R is alkyl, alkenyl, alkynyl, aryl, or aralkyl, containing from 0–20 heteratoms;

$R_4$ and $R_8$ are alkyl, alkenyl, alkynyl, aralkyl, or alkoxyl;

X is an anion, preferably CH$_3$SO$_4^-$, OSO$_2$F$^-$, halide,

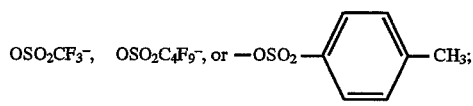

wherein R is as defined above; Q is

—O—, —S—, —NH—, —C—, —SO$_3$—,
              ‖
              O diazo,

—NHCNH—, NHCNH—, —NHCO—,
   ‖        ‖         ‖
   S        O         O

—NHC—, —CNH—, or —NHC  ;
   ‖      ‖         ‖
   O      O        $^+$NH$_2$

I is an ionizable group; and n is at least 1.

Preferably $R_1$ is alkyl, alkenyl, alkynyl, aryl or aralkyl of from 1 to 24 carbon atoms;

$R_2$, $R_3$, $R_5$ and $R_7$ are hydrogen, amino, —COOH, cyano, hydroxyl, alkoxyl of from 1 to 4 carbon atoms, nitro, halide, —SO$_3$, or —SCN;

$R_4$ and $R_8$ are preferably or alkyl, alkenyl, alkynyl, or alkoxyl, of from 1 to 8 carbon atoms; X is halide; $R_6$ is —Q—R—I$_{(n)}$; Q is

—O—, —S—, —NH—, —C—,
              ‖
              O diazo,

—NHCNH—, —NHCNH—, —NHC—,
   ‖        ‖         ‖
   O        S         O

—NHCO—, —CNH—, or —NHC—;
   ‖       ‖        ‖
   O       O       $^+$NH$_2$ and R is alkyl, alkenyl, alkynyl, aryl, or aralkyl, of from 1 to 24 carbon atoms, containing from 0 to 20 heteratoms selected from the group consisting of nitrogen, oxygen, phosphorous, and sulfur.

An ionizable group for the purposes of this invention is any functional group which retains a net positive or negative charge within a specific pH range. Preferably the functional group will retain a net positive or negative charge within the range of pH2–10 and, more preferably, within the range of pH5–9. I can be any ionizable group provided that the ionizable group is not deleterious to the encapsulation of the acridinium ester of this invention within the liposome. I is preferably —SO$_3$H, —OSO$_3$H, —POCOH)$_2$ or —OPO$_3$ (OH), and n is preferably about 1 to about 20 and, more preferably, less than about 10.

More preferably, $R_1$ is alkyl of from 1 to 10 carbon atoms; $R_2$, $R_3$, $R_5$, and $R_7$ are hydrogen, nitro, —CN, halide, alkoxyl of from 1 to 4 carbon atoms, amino, or —SO$_3$H; and $R_4$ and $R_8$ are alkyl of from 1 to 4 carbon atoms.

Most preferably, $R_1$, $R_4$, and $R_8$ are methyl; $R_2$, $R_3$, $R_5$, and $R_7$ are hydrogen; X is bromide; $R_6$ is —Q—R—I$_{(n)}$, Q is a

and —R—I$_{(n)}$ is selected from the group consisting of aminomethanesulfonic acid, 7-amino-1,3-naphthalenedisulfonic acid, S-(3-sulfopropyl)cysteine, 2-aminoethyl hydrogen sulfate, 2-aminoethylphosphonic acid, and 2-aminoethyl dihydrogen phosphate.

The $R_5$ and $R_6$ position can be interchanged in the acridinium esters of this invention. Accordingly, the preferred acridinium esters of this invention include acridinium esters of the following formula:

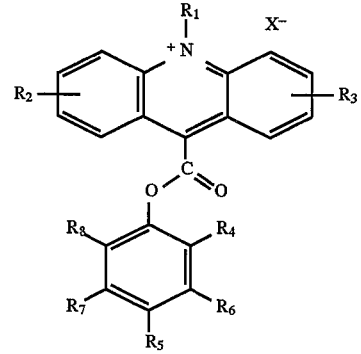

wherein $R_1$, $R_2$, $R_3$, $R_4$, $R_5$, $R_6$, $R_7$, $R_8$, and X are as defined above.

The novel acridinium esters of the present invention are highly soluble in water and can be encapsulated in liposomes at high concentrations. Once inside liposomes, the novel acridinium esters remain encapsulated for extended periods of time and do not leak appreciably.

It will be appreciated that although the novel acridinium esters of the present invention have been described with respect to their usefulness with liposomes, the novel acridinium esters of the present invention are also useful in other applications where acridinium esters are utilized, such as labeling ligands or analytes (such as antigens); labeling the specific binding partners of ligands or analytes (such as the corresponding antibodies); or labelling nucleic acids and molecules comprising nucleic acids.

Lumisomes useful in this invention can be prepared by any of the various known methods for producing either unilamellar liposome vesicles or multilamellar liposome vesicles. Lumisomes are single or multicompartmented bodies obtained when lipids or lipid mixtures are dispersed in an aqueous suspension containing the acridinium esters useful in this invention.

As an example of one method for producing lumisomes, lipids are dissolved in a suitable organic solvent, such as chloroform, and placed into a suitable vessel. A dry film of lipids is formed on the interior surface of the vessel by evaporation of the organic solvent. The aqueous solution containing the acridinium esters to be entrapped within the lumisomes is then placed in the vessel in contact with the lipid film. The lipid film is then dispersed in the aqueous solution by vigorous agitation or sonication.

Numerous other methods exist for forming liposomes which are useful for producing the lumisomes useful in this invention and it is left to the artisan to choose the method best suited for a desired use. A preferred method for manufacturing liposomes is disclosed in copending U.S. application Ser. No. 940,519, filed on Dec. 10, 1986, now U.S. Pat. No. 4,933,121 herein incorporated by reference.

The lnmisome can be derivatized with a ligand, ligand analog, or anti-ligand using known procedures in the art. Depending on the intended use of the lumisome, the ligand, ligand analog, or anti-ligand can be an antigen, hapten, antibody, nucleic acid, DNA, RNA, avidin or other receptor.

The lumisomes so formed can be used as tracers in assays in which an analyte in a sample fluid is to be detected. The type of assay utilized and/or the analyte to be detected will determine the ligand, ligand analog or anti-ligand used to form the lumisome. For example, if a competitive assay is used for determining an antigen or hapten, the ligand or ligand analog employed will be either the analyte or its analog.

If a sandwich assay is to be used the ligand, ligand analog or anti-ligand employed would be specific for the analyte to be assayed. For example, an antibody, such as a monoclonal antibody, elicited in response to the analyte to be assayed, could be used to derivatize the lumisome.

An example of an assay for detecting a DNA or RNA probe using the lumisomes of this invention is as follows: The DNA or RNA probe is tagged with a ligand such as a hapten or a biotinylated modified nucleotide. The DNA or RNA probe is allowed to hybridize with complementary DNA or RNA and immobilized on a solid support. The immobilized probe is then reacted with lumisomes comprising a receptor for the ligand, such as an antibody or if the probe is biotinylated, avidin. The lumisomes are ruptured and the amount of signal generated by the encapsulated acridinium ester is measured.

Alternatively, a receptor can be utilized which recognizes and binds to the probe/complementary DNA or RNA hybrid, in the absence of a tag, such as an anti-hybrid antibody.

The following Examples are presented to illustrate the present invention.

EXAMPLE 1

Preparation of 2',6'-Dimethyl-4'-carboxyphenyl 10-methyl-acridinium-9-carboxylate bromide (DMAE-COOH)

A mixture of 2',6'-dimethyl-4'-benzyloxycarbonylphenyl 10-methyl-acridinium-9-carboxylate methosulfate (7.9, 13.4 mmole) (prepared as described in U.S. Pat. No. 4,745,181), 150 ml of glacial acetic acid and 46 ml of 48% hydrogen bromide was heated at 100°–105° C. for 3 hours and then left at room temperature overnight. 400 ml of anhydrous ethyl ether was added to the mixture to form a second mixture which was then refrigerated 3 days. The second mixture was then filtered to produce a yellow crystalline residue. The residue was washed with anhydrous ethyl ether and air dried.

EXAMPLE 2

Preparation of 2',6'-Dimethyl-4'-(sulfomethylcarbamoyl) phenyl 10-methyl-acridinium-9-carboxylate bromide (DMAE-AMS)

A solution of 2',6'-dimethyl-4'-carboxylphenyl 10-methyl-acridinium-9-carboxylate bromide (DMAE-COOH, 20 mg, 0.043 mmole) in 2 ml of dimethylformamide (DMF)/CHCl$_3$ (1:1) was cooled in an ice bath, treated with triethylamine (31 ul, 0.215 mmole) and ethyl chloroformate (6.1 ul, 0.065 mmole) to form a reaction mixture. After 30 min. the reaction mixture was evaporated. The residue of the evaporation was reconstituted in 2 ml of DMF, treated with triethylamine (31 ul, 0.215 mmole) and aminomethane-sulfonic acid (9.5 mg, 0.086 mmole) to form a second reaction mixture. The second reaction mixture was stirred at room temperature overnight, and evaporated. The crude product so formed was purified on one analytical TLC plate (Silica gel 60, F254, Merck & Co., Inc., Rahway, N.J.), and developed with chloroform/methanol/water (65:25:4). The yellow band which developed on the plate (Rf=0.38) (which could also be detected under both long and short UV light) was stripped from the plate and eluted with the same solvent system. The eluent so produced was evaporated and the residue of the evaporation triturated with methanol to form a mixture. This mixture was then filtered through a polycarbonate membrane (13 mm diameter, 0.2 um pore size) (Nucleopore Corp., Pleasanton, Calif.) mounted on a syringe filter holder, and the filtrate so produced was evaporated to give DMAE-AMS (15 mg, 62%).

EXAMPLE 3

Preparation of 2',6'-Dimethyl-4'-[N-7-(1,3-disulfonaphthalenyl)carbamoyl]phenyl 10-methyl-acridinium-9-carboxylate Bromide (DMAE-ANDS)

A solution of 2',6'-dimethyl-4'-carboxylphenyl 10-methyl-acridinium-9-carboxylate bromide (DMAE-COOH, 18 mg, 0.038 mmole) in 3.6 ml of a dioxane/water (1:1) mixture was treated with 1-(3-dimethylaminopropyl)-3-ethylcarbodiimide hydrochloride (37 mg, 0.193 mmole, Aldrich Chemical Co., Inc., Milwaukee, Win.) at room temperature for 5 minutes to form a reaction mixture. A solution of 7-amino-1,3-naphthalenedisulfonic acid (ANDS, 26 mg, 0.076 mmole, Aldrich Chemical Co., Inc.) in 0.9 ml of water was added to the reaction mixture which was then stirred at room temperature overnight and evaporated.

The residue of the evaporation was dissolved in a minimal amount of 0.1M sodium carbonate to obtain a solution at neutral pH. This solution was mixed with an equal amount of methanol and purified on a 20×20cm preparative TLC plate (Silica gel 60, F254, Merck & Co., Inc.), and developed with chloroform/methanol/water (55:40:5). The yellow band which developed (Rf=0.4) was treated in the same manner as the yellow band described in Example 1 to give DMAE-ANDS (15 mg, 50%). Fast Atom Bombardment (FAB) Mass Spectral Analysis (by Oneida Research Services, Whitesboro, N.Y.) in the positive ion mode gave a M+ peak of 671, a M+Na peak of 693, and a M+2Na peak of 715. A bromide peak of 80 was detected in the negative ion mode.

EXAMPLE 4

Preparation of 2',6'-Dimethyl-4'-{N-[1-carboxyl-2-(3-sulfopropylthio)ethyl]carbamoyl}phenyl 10-methyl-acridinium-9-carboxylate bromide (DMAE-SCYS)

A solution of 2',6'-dimethyl-4'-carboxylphenyl 10-methyl-acridinium-9-carboxylate bromide (DMAE-COOH, 50 mg, 0.107 mmole) in 10 ml of DMF/CHCl$_3$ (1:1) was cooled in an ice bath, treated with triethylamine (77 u., 0.535 mmole) and ethyl chloroformate (20 ul, 0.214 mmole) to form a reaction mixture. After 30 min. the reaction mixture was evaporated. The residue of the evaporation was reconstituted in 10 ml of DMF/CHCl$_3$ (1:1), treated with triethylamine (77 u., 0.535 mmole), and S-3-sulfopropyl-L-cysteine (51 mg, 0.214 mmole) (prepared by the method of U.T. Ruegg and J. Rudinger, J. Peptide Protein Res. 6, 447, 1974) to form a second reaction mixture. The second reaction mixture was heated at 60° C.–70° C. overnight, and evaporated.

The residue of the evaporation was purified on one 20×20 cm preparative TLC plate (Silica gel 60, F254, Merck & Co., Inc.), developed with chloroform/methanol/water (55:40:5). The yellow band which developed (Rf=0.4) (which could also be detected under both long and short UV light) was treated in the same manner as the yellow band described in Example 1 to give the DMAE-SCys (37 mg, 36%).

FAB Mass Spectral Analysis in the positive ion mode gave a M+ peak of 611, a M+Na peak of 633, and a M+Na,K peak of 673.

EXAMPLE 5

Preparation of 2',6'-Dimethyl-4'-[N-(2-sulfonyloxyethyl) carbamoyl]phenyl 10-methyl-acridinium-9-carboxylate bromide (DMAE-AEOS)

A solution of 2',6'-dimethyl-4'-carboxylphenyl 10-methyl-acridinium-9-carboxylate bromide (DMAE-COOH, 35 mg, 0.075 mmole) in 5 ml of DMF was cooled in an ice bath, treated with triethylamine (44 ul, 0.31 mmole) and ethyl chloroformate (8.5 ul, 0.090 mmole). After 20 minutes, aminoethyl hydrogen sulfate (Aldrich, 30 mg, 0.21 mmole) was added to form a reaction mixture, and the ice bath removed. The reaction mixture was stirred at room temperature overnight and evaporated. The residue of the evaporation was triturated with 5 ml of a chloroform/methanol/water (73:24:3) mixture, and filtered to remove the insoluble materials. The filtrate so produced was concentrated, purified on a 20×20 cm preparative TLC plate (Silica gel 60, F254, Merck & Co., Inc.) and developed with chloroform/methanol/water (65:25:4). The yellow band which developed (Rf=0.48) (which could also be detected under both long and short UV light) was treated in the same manner as the yellow band described in Example 1 to give DMAE-AEOS (14 mg, 32%).

EXAMPLE 6

Preparation of 2',6'-Dimethel-4'-[N-(2-phosphonoethyl) carbamoyl]phenyl 10-methyl-acridiniUm-9-carboxylate bromide (DMAE-AEP)

A solution of 2',6'-dimethyl-4'-carboxylphenyl 10-methyl-acridinium-9-carboxylate bromide (DMAE-COOH, 100 mg, 0.215 mmole) in 20 ml of 25% DMF in chloroform was cooled in an ice bath, treated with triethylamine (180 ul, 1.30 mmole) and ethyl chloroformate (62 ul, 0.65 mmole) to form a reaction mixture. After 30 minutes, the reaction mixture was evaporated. The residue of the evaporation was reconstituted in 12 ml of DMF. To this solution so formed was added triethylamine (300 ul, 2.15 mmole) and 2-aminoethylphosphonic acid (80 mg, 0.64 mmole, Aldrich Chemical Co., Inc.) in 5 ml of water to form a second reaction mixture. The second reaction mixture was stirred at room temperature overnight and evaporated. The residue of the evaporation was taken up in 2–3 ml of chloroform/methanol/water (73:24:3), purified on one 20×20 cm preparative TLC plate (Silica gel 60, F254, Merck & Co., Inc.) and developed with chloroform/methanol/water (65:25:4). The yellow band which developed on the plate (Rf=0.45) (which can be detected also under long and short UV light) was treated in the same manner as the yellow band described in Example 1 to give DMAE-AEP (72 mg, 58%).

FAB Mass Spectral analysis in the positive ion mode gave a M+ peak of 493 and a M+Na peak of 515.

EXAMPLE 7

Preparation of 2',6'-Dimethyl-4'[N-(2-phosphonooxyethyl) carbamoyl]phenyl 10-methyl-acridinium-9-carboxylate bromide (DMAE-AEOP)

A solution of 2',6'-dimethyl-4'-carboxylphenyl 10-methyl-acridinium-9-carboxylate bromide (DMAE-COOH, 100 mg., 0.215 mmole) in 20 ml of 25% DMF in chloroform was cooled in an ice bath, treated with triethylamine (180 ul, 1.30 mole) and ethyl chloroformate (62 ul, 0.65 mmole) to form a reaction mixture. After 30 minutes, the reaction mixture was evaporated. The residue of the evaporation was reconstituted in 12 ml of DMF. To this solution so formed was added triethylamine (300 ul, 2.15 mmole) and 2-aminoethyl dihydrogen phosphate (91 mg, 0.64 mmole, Aldrich Chemical Co., Inc.) in 5 ml of water to form a second reaction mixture. The second reaction mixture was stirred at room temperature overnight and evaporated. The residue of this evaporation was taken up in 2–3 ml of chloroform/methanol/water (73:24:3), purified on one 20×20 cm preparative TLC plate (Silica gel 60, F254, Merck & Co., Inc.) and developed with chloroform/methanol/water (65:25:4). The yellow band which developed (Rf=0.45) (which could also be detected also under long and short UV light) was treated in the same manner as the yellow band described in Example 1 to give DMAE-AEOP. (100 mg: 79%). FAB Mass Spectral analysis in the positive ion mode gave a M+ peak of 509.

EXAMPLE 8

Rate of Leakage of Acridinium Esters From Lumisomes

Lumisomes were prepared as follows:

Chloroform solutions containing 25 mg dipalmitoyl phosphatidylcholine, 13.5 mg cholesterol, and 2.2 mg dipalmitoyl phosphatidylglycerol were air-dried on a round flat glass dish, 7 cm in diameter, and were placed for 16 hours in a vacuum to produce dry lipid films. Acridinium esters DMAE-COOH, DMAE-AMS, and DMAE-ANDS, were each dissolved in a solution of 0.215M sucrose, 0.25 mM EDTA, pH 7 (0.1–0.26 mg/ml). Acridinium esters DMAE-SCYS, DMAE-AEOS, DMAE-AEP, and DMAE-AEOP, were each dissolved in a solution of 50 mM sodium phosphate, pH 7.4 (0.1–0.26 mg/ml). A three ml aliquot of each acridinium ester solution so formed was added to a separate dry lipid film and gently mixed at 45° C. for 10 min. to produce a lumisome suspension. Each suspension so formed containing DMAE-COOH, DMAE-AMS, and DMAE-ANDS, was extruded through polycarbonate membranes with a pore size of 0.4 and 0.2 microns and then washed 4 times by ultracentrifugations at 45,000 rpm for 30 min. in TRIS Buffer (0.1M TRIS, 0.03M NaCl, 0.01% $NaN_3$, 0.5 mM EDTA, pH 7.8) to produce a lumisome pellet. The lumisome pellets so formed were each resuspended in 10 ml of TRIS Buffer. Each lumisome suspension containing DMAE-SCYS, DMAE-AEOS, DMAE-AEP, and DMAE-AEOP, was extruded through polycarbonate membranes with a pore size of 0.4 and 0.2, microns and then washed 4 times by ultracentrifugation at 45,000 rpm for 30 min. in 50 mM sodium phosphate, pH 7.4, to produce a lumisome pellet. The lumisome pellets so formed were each resuspended in 10 ml of 50 mM sodium phosphate, pH 7.4. A sample of each resuspended lumisome pellet was mixed with 0.1% TRITON X-100 detergent (weight/volume) for determination of the total amount of encapsulated acridinium ester. Aliquots of each of the resuspended lumisome pellets were incubated for 7 days at 4° C. and 37° C. The aliquots were then centrifuged at 45,000 rpm for 2 hours. After centrifugation, a sample was taken from each supernatant and mixed with 0.1% TRITON X-100. The concentration of acridinium ester in each supernatant was then measured using the Ciba Corning Magic® LITE Analyzer (Ciba Corning Diagnostics Corp., Medfield, Mass.). The percent leakage of acridinium ester was then calculated by comparing the amount of acridinium ester in the supernatant to the total amount of acridinium ester originally encapsulated within the lumisomes.

TABLE 1

| Acridinium Ester | % Leakage at 4° C./7 Days | % Leakage at 37° C./7 Days |
| --- | --- | --- |
| DMAE-COOH | 25.0% | 36.0% |
| DMAE-AMS | 0.8% | 26.0% |
| DMAE-ANDS | 1.3% | 1.9% |
| DMAE-SCYS | 0.5% | 4.9% |
| DMAE-AEOS | 1.4% | 52.8% |
| DMAE-AEP | 0.3% | 1.0% |
| DMAE-AEOP | 1.8% | 1.7% |

EXAMPLE 9

Effect of Different Buffers on Acridinium Ester Leakage From Lumisomes

Lumisomes encapsulating DMAE-ANDS were prepared according to the procedure described in Example 8 except that the DMAE-ANDS was dissolved in the four buffers listed in Table 2, prior to addition to the dry lipid film. The buffers were then used to wash, resuspend and store, respectively, the four lumisome prepartions in Table 2. The lumisomes so prepared were stored in their respective buffers for 35 days at either 4° C. or 37° C. and then centrifuged at 45,000 rpm for 2 hours. The concentration of DMAE-ANDS in each supernatant was then measured using a Ciba Corning Magic® LITE Analyzer. The percent leakage of DMAE-ANDS was then calculated by comparing the amount of DMAE-ANDS in the supernatant versus the amount of DMAE-ANDS originally encapsulated within the lumisomes.

TABLE 2

Effect of Different Buffers on the Leakage of DMAE-ANDS from Lumisomes After 35 Days at 4° C. and at 37° C.

| Buffer (50 mM) | % Leakage at 4° C. | % Leakage at 37° C. |
| --- | --- | --- |
| Sodium phosphate pH 7.4 | 0.35% | 0.85% |
| Sodium acetate pH 7.4 | 0.33 | 1.39 |
| Sodium tartarate pH 7.4 | 0.62 | 1.30 |
| Sodium HEPES pH 7.4 | 0.79 | 1.71 |

EXAMPLE 10

Total $T_4$ Assay

A. Reagent Preparation

Thyroxine ($T_4$) lumisomes encapsulating DMAE-AMS were prepared as described in Example 8 except that 0.16 mg of dipalmitoyl-phosphatidylethanolamine-succinyl-thyroxine (prepared as described in U.S. application Ser. No. 094,667, filed on Sep. 9, 1987, herein incorporated by reference) was added to the lipid mixture. DMAE-AMS at 0.2 mg/ml in phosphate buffer was used for hydration of the lipid film. The lumisome thus formed with the attachment of a hapten, thyoxine, is hereby referred to as a luminescent conjugate. The final lumisome preparation was diluted in Buffer A (0.02M Tris, 0.1M NaCl, 0,001M EDTA, 0.1% bovine serum albumin (BSA), 0.1% sodium azide, pH 7.8).

Monoclonal anti-$T_4$ antibody was produced in mice (A/J) by immunization with a BSA-$T_4$ conjugate and subsequent fusion of the splenocytes with Sp2/0-Ag 14 myeloma cells by the procedure described byKohler and Milstein in Nature (London), Vol. 256, pp. 495–497 (1975). Hybridoma cells secreting anti-$T_4$ antibody were detected by radioimmunoassay using the following procedure: Supernatant from the cells were diluted 1:5 in phosphate buffered saline containing 0.1% (weight/volume) bovine gamma globulin. 100 ul of each diluted supernatant and 100 ul of $^{125}$I-labelled $T_4$ were added to a test tube and were incubated. for one (1) hour at room temperature. Goat anti-mouse IgG coupled to paramagnetic particles were added to each tube for ten (10) minutes at room temperature. The particles were magnetically separated and counted. The cells that tested positive (i.e., produced counts over background) were plated at 0.1 cell/well and then retested after growth.

Cells resulting from this regrowth which tested positive were then injected introperitoneally into pristane-primed mice (CAF). Ascitic fluid from these mice was collected after 3–5 weeks. The anti-$T_4$ antibody was purified from the ascitic fluid by Protein A column chromatography using the Affi-Gel Protein A MAPS II Kit (Bio-Rad Laboratories, Richmond, Calif.) according to the written protocol provided by the kit. The anti-$T_4$ antibody was immobilized on paramagnetic particles as described by Groman et al, BioTechniques 3:156–160 (1985). The antibody-derivatized particles were diluted to a concentration of 50 ug of particles per 0.1 ml of Buffer B (0.03M phosphate, 0.1M NaCl, 2.9 mg/ml merthiolate, and 0.1% BSA, 0.1% sodium azide, pH 7.4).

B. Assay procedure

A series of standards (0.05 ml) with known increasing amounts of $T_4$ were added to 12×75mm plastic tubes. 0.1 ml of the T$_4$-lumisomes prepared in A containing 10×10$^6$ RLU (relative light units) in Buffer A were then added, followed by the addition of 0.5 ml of the paramagnetic-particles immobilized with monoclonal anti-T$_4$ antibody as prepared in A. The tubes were incubated for 1 hour at room temperature and then placed in a magnetic field of a specially designed rack useful for magnetic separation of paramagnetic particles in test tubes (available from Ciba Corning Diagnostics Corp., Medfield, Mass.). The magnetic field separated the particles from the supernatant and the supernatant was then decanted. The particles were washed once in 1 ml of phosphate-buffered saline, vortexed, and magnetically separated. The particles were resuspended in 0.1 ml of TRITON X-100, 0.1% (w/v) in deionized water.

The tubes were then placed in a luminometer (MAGIC® LITE Analyzer, Ciba Corning Diagnostics Corp., Medfield, Mass.). 0.3 ml of a solution of 0.1% hydrogen peroxide in 0.1N HNO$_3$ was added to each tube by the luminometer and the light emission was triggered by the addition of 0.3 ml of 0.25N NaOH containing ARQUAD surfactant (Armark Chemicals, Chicago, Ill.). The measured RLU for each tube was plotted against its respective T$_4$ concentration as shown in FIG. 1.

EXAMPLE 11

Free T$_4$ Assay

Figure 2:
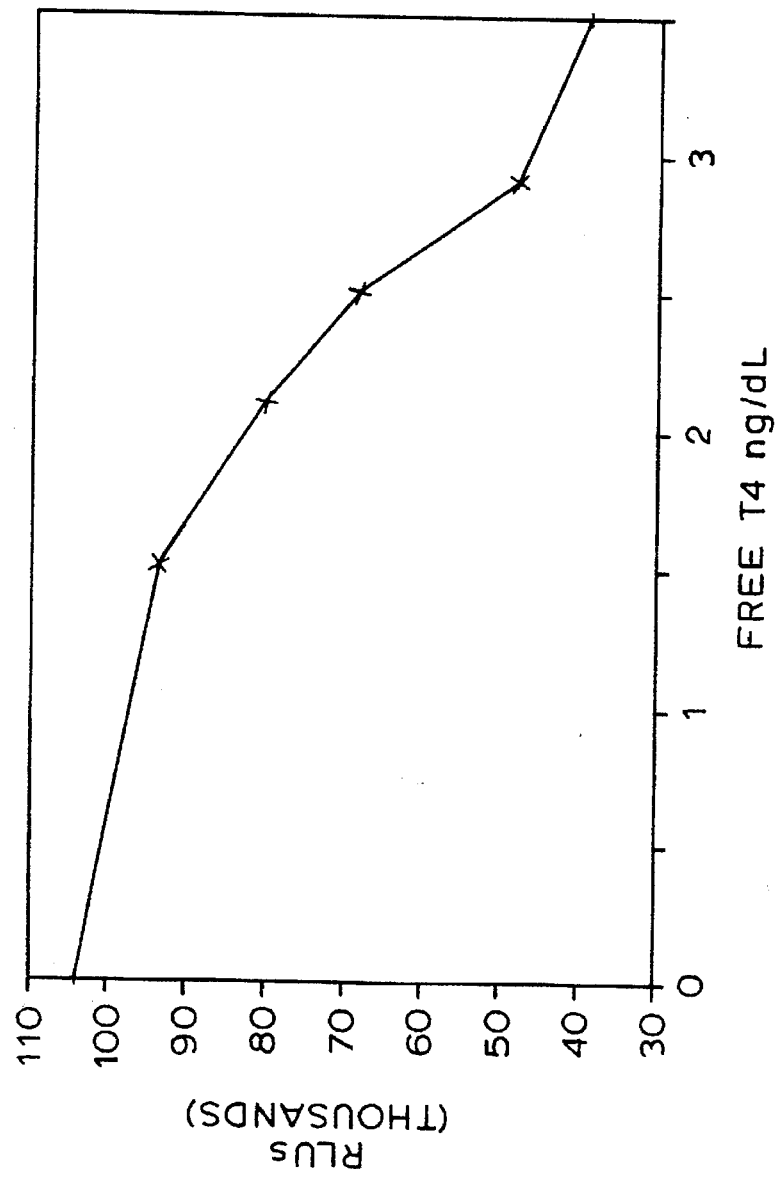
FIG. 2 is a standard curve for a Free $T_4$ Assay using lumisomes of this invention

A series of serum-based standards containing known increasing concentrations of free T$_4$ were added to 12×75 mm plastic tubes. 0.1 ml of the T$_4$-lumisomes prepared in Example 10A containing 10×10$^6$ RLU was added, followed by the addition of 0.5 ml of the paramagnetic-particles immobilized anti-T$_4$ antibody as prepared in Example 10A, in Buffer B minus merthiolate. The reaction was carried out for 1 hour at room temperature and the tubes were further processed and read as in Example 10. FIG. 2 shows the standard curve obtained by plotting the measured RLU for each tube against its respective free T$_4$ concentration.

EXAMPLE 12

Creatine kinase MB (CKMB) Assay

A. Reagent preparation

Monoclonal antibodies to creatine kinase MB (CKMB) and creatine kinase BB (CKBB) were prepared as described by Piran et al, Clinical Chemistry 33:1517–1520 (1987).

Lumisomes were prepared as described in Example 8, except that 1 mg dithiopyridyl dipalmitoyl phosphatidylethanolamine (DTP-DPPE), prepared according to Barbet et al, J. Supramolecular Structure 16:243–258 (1981), was added to the lipid mixture. The dry lipid film was hydrated with DMAE-ANDS, 2 mg/ml, and the final lumisome preparation was diluted in 0.1M sodium phosphate, 0.15M NaCl, and 0.005M EDTA, pH 7.5.

The anti-CKMB monoclonal antibody was coupled to the DTP-DPPE containing lumisomes by the method of Barbet et al J. Supromolecular Structure 16:243–258 (1981). The anti-CKMB antibody bearing lumisomes were diluted in Buffer C (0.1M 1,4-piperazinediethanesulfonic acid, 0.15M NaCl, 0.001M EDTA, 0.1% NAN$_3$, 0.1% BSA, pH 6.5). "The "anti-CKMB antibody bearing lumisomes" which is described in this paragraph is called a luminescent conjugate."

The anti-CKBB monoclonal antibody was immobilized on paramagnetic particles as described in Example 10 for the anti-T$_4$antibody and diluted in Buffer C to a final concentration of 100 ug of particles per ml of Buffer C.

B. Assay procedure

Figure 3:
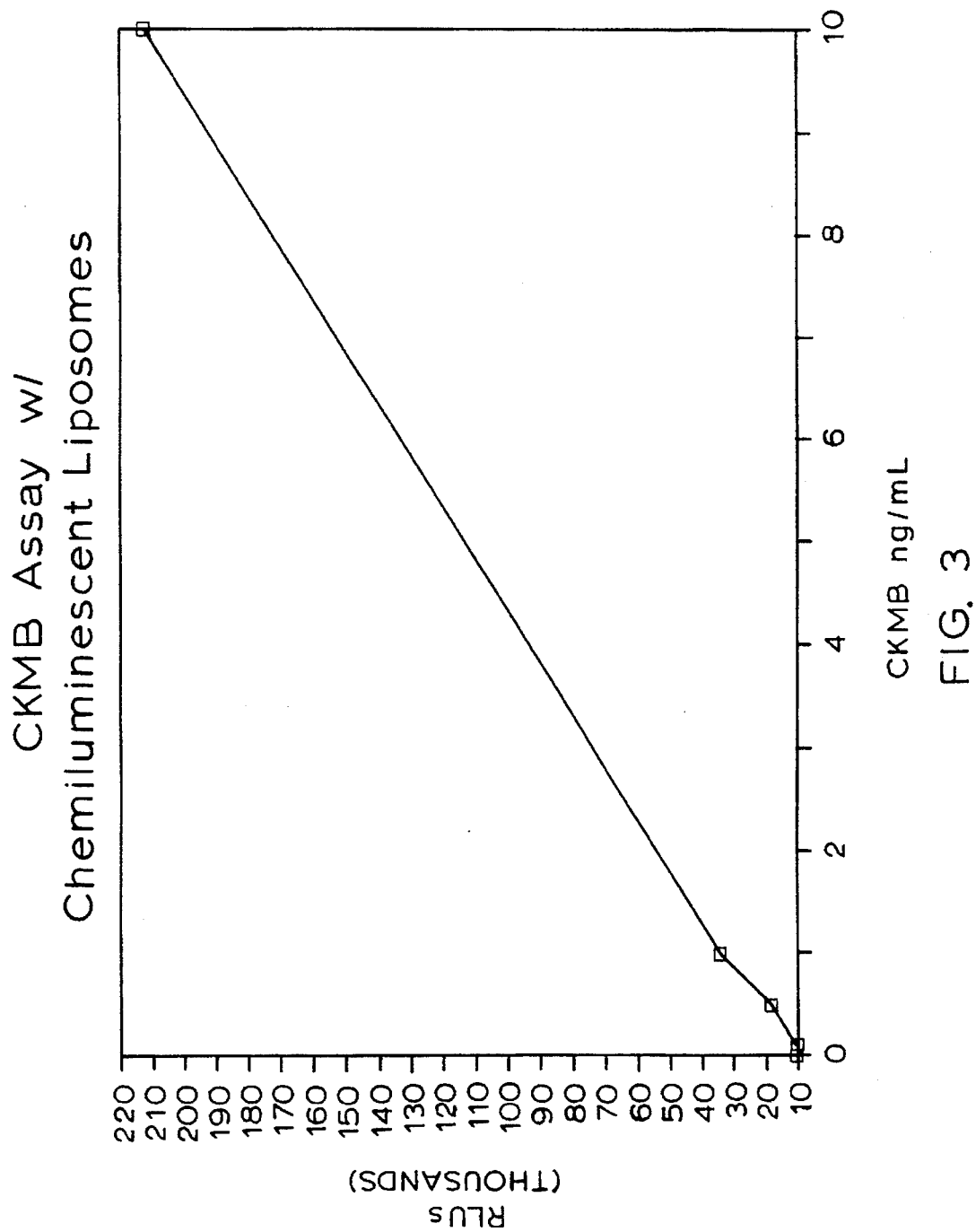
FIG. 3 is a standard curve for a CKMB Assay using lumisomes of this invention.

A series of serum-based standards (0.1 ml) with known increasing concentrations of human cardiac CKMB were added to 12×75 mm plastic tubes. 0.1 ml of the anti-CKMB antibody bearing lumisomes prepared in A containing 10×10$^6$ RLU was added to each tube and the tubes were then incubated for 30 minutes at room temperature. To each tube was then added 50 ug of the anti-CKBB antibody bearing paramagnetic-particles prepared in A and the the tubes were incubated for another 30 minutes at room temperature. The tubes were then processed and read as in Example 10, except that Buffer C minus BSA was used in the wash step instead of phosphate-buffered saline. The measured RLU for each tube was plotted against its respective CKMB concentration as shown in FIG. 3.

C. Four samples of human sera were assayed using the procedure described in B and concentrations of <1, 21, 24 and 68 ng/ml CKMB respectively, were determined. When these four samples were assayed using the CKMB Magic® LITE Assay (Ciba Corning Diagnostics Corp., Medfield, Mass. 02052), CKMB values of <1, 18, 24 and 72 ng/ml, respectively were determined, indicating good agreement between the two assays.

EXAMPLE 13

Thyroid Stimulating Hormone (TSH) Assay

A. Reagent preparation

Anti-TSH monoclonal antibodies were produced from TSH-immunized mice as described in Example 10 for the preparation of anti-T$_4$ antibodies. Preparation of DTP-DPPE containing lumisomes loaded with DMAE-ANDS and paramagnetic particles-immobilized anti-TSH was done as described in Example 12. These reagents were diluted in Buffer C.

B. Assay procedure

A series of serum-based standards (0.1 ml) with known increasing concentrations of TSH were added to 12×75 mm plastic tubes. 0.1 ml of the anti-TSH antibody bearing lumisomes prepared in A containing 8×10$^6$ RLU were added and the tubes were then incubated for 2 hours at room temperature. Paramagnetic-particles immobilized anti-TSH antibody as prepared in A was then added (0.5 ml) and the tubes were then incubated for an additional 30 minutes at room temperature. The tubes were then processed and read as described in Example 11.

C. The TSH assay was performed by the same procedure as described in B, except that the anti-TSH antibody bearing lumisomes were replaced by the anti-TSH antibody prepared in A labeled directly with 2',6'-dimethyl-4'-(N-succinimidyloxycarbonyl)phenyl 10-methyl-acridinium-9-carboxylate methosulfate (DMAE-NHS).

Figure 4:
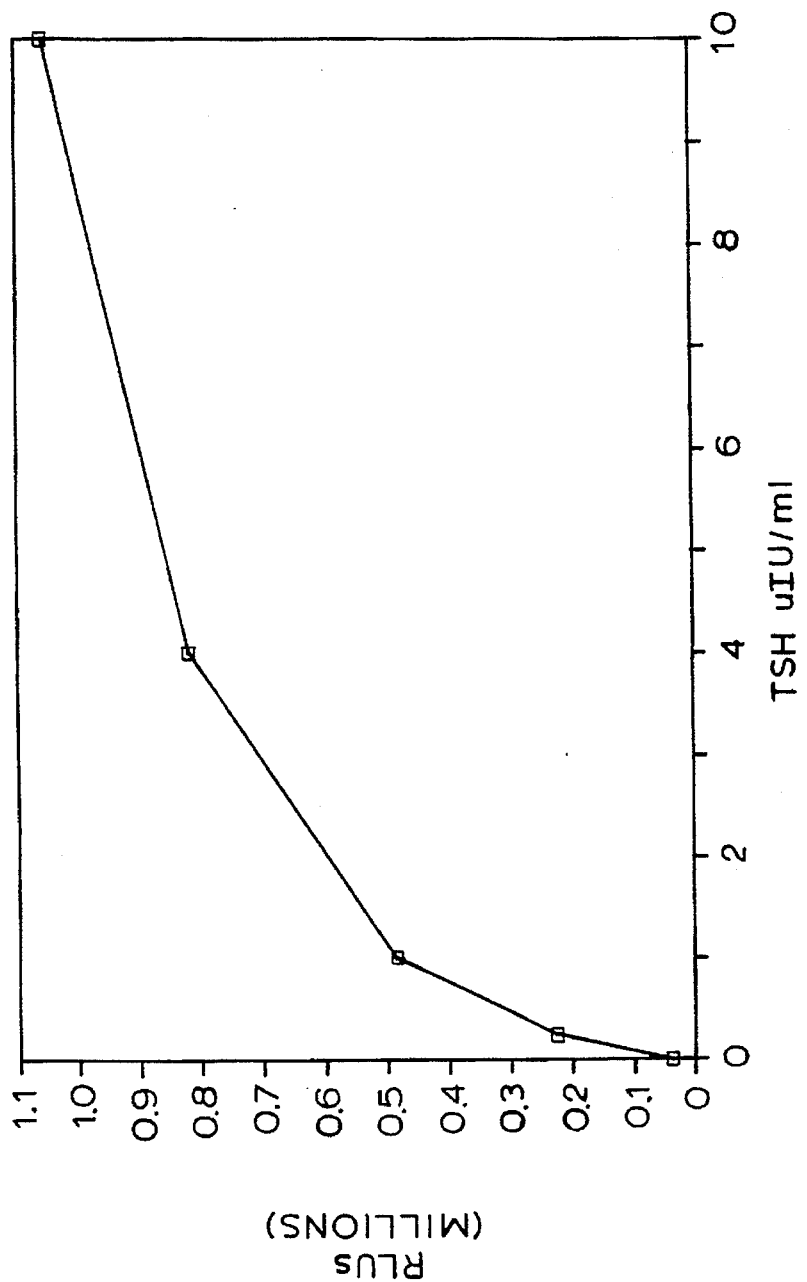
FIG. 4 is a comparison of two standard curves for a TSH Assay, the top curve respresenting a TSH assay using lumisomes of this invention and the bottom curve representing a TSH assay using antibody directly labeled with acridinium ester.

D. The standard curves obtained by the procedures described in B and C using the two types of labels are shown in FIG. 4. The results indicate that by using lumisomes encapsulating the hydrophilic acridinium ester analogue as the label, the signal to noise ratio at the low end of the assay is significantly increased. This increase in signal to noise ratio is advantageous because it allows better assay sensitivity, precision and speed.

E. The assay described in B was conducted using shorter incubation times (see FIG. 5). It was found that even when the first incubation time was 2.5 minutes and the second incubation time was also 2.5 minutes the sensitivity of the assay was satisfactory. It was not possible to obtain a sufficiently sensitive standard curve using the anti-TSH antibody which had been labeled directly with DMAE-NHS using the short incubation times. Surprisingly, the signal to respect to their usefulness with liposomes, the novel acridinium esters of the present invention are also useful in other applications where acridinium esters are utilized, such as labeling ligands or analytes (such as antigens); labeling the specific binding partners of ligands or analytes (such as the corresponding antibodies); or labelling nucleic acids and molecules comprising nucleic acids.

Lumisomes useful in this invention can be prepared by any of the various known methods for producing either unilamellar liposome vesicles or multilamellar liposome vesicles. Lumisomes are single or multicompartmented bodies obtained when lipids or lipid mixtures are dispersed in an aqueous suspension containing the acridinium esters useful in this invention.

As an example of one method for producing lumisomes, lipids are dissolved in a suitable organic solvent, such as chloroform, and placed into a suitable vessel. A dry film of lipids is formed on the interior surface of the vessel by evaporation of the organic solvent. The aqueous solution containing the acridinium esters to be entrapped within the lumisomes is then placed in the vessel in contact with the lipid film. The lipid film is then dispersed in the aqueous solution by vigorous agitation or sonication.

Numerous other methods exist for forming liposomes which are useful for producing the lumisomes useful in this invention and it is left to the artisan to choose the method best suited for a desired use. A preferred method for manufacturing liposomes is disclosed in copending U.S. application Ser. No. 940,519, filed on Dec. 10, 1986, now U.S. Pat. No. 4,933,121 herein incorporated by reference.

The lnmisome can be derivatized with a ligand, ligand analog, or anti-ligand using known procedures in the art. Depending on the intended use of the lumisome, the ligand, ligand analog, or anti-ligand can be an antigen, hapten, antibody, nucleic acid, DNA, RNA, avidin or other receptor.

The lumisomes so formed can be used as tracers in assays in which an analyte in a sample fluid is to be detected. The type of assay utilized and/or the analyte to be detected will determine the ligand, ligand analog or anti-ligand used to form the lumisome. For example, if a competitive assay is used for determining an antigen or hapten, the ligand or ligand analog employed will be either the analyte or its analog.

If a sandwich assay is to be used the ligand, ligand analog or anti-ligand employed would be specific for the analyte to be assayed. For example, an antibody, such as a monoclonal antibody, elicited in response to the analyte to be assayed, could be used to derivatize the lumisome.

An example of an assay for detecting a DNA or RNA probe using the lumisomes of this invention is as follows: The DNA or RNA probe is tagged with a ligand such as a hapten or a biotinylated modified nucleotide. The DNA or RNA probe is allowed to hybridize with complementary DNA or RNA and immobilized on a solid support. The immobilized probe is then reacted with lumisomes comprising a receptor for the ligand, such as an antibody or if the probe is biotinylated, avidin. The lumisomes are ruptured and the amount of signal generated by the encapsulated acridinium ester is measured.

Alternatively, a receptor can be utilized which recognizes and binds to the probe/complementary DNA or RNA hybrid, in the absence of a tag, such as an anti-hybrid antibody.

The following Examples are presented to illustrate the present invention.

EXAMPLE 1

Preparation of 2',6'-Dimethyl-4'-carboxyphenyl 10-methyl-acridinium-9-carboxylate bromide (DMAE-COOH)

A mixture of 2',6'-dimethyl-4'-benzyloxycarbonylphenyl 10-methyl-acridinium-9-carboxylate methosulfate (7.9, 13.4 mmole) (prepared as described in U.S. Pat. No. 4,745,181), 150 ml of glacial acetic acid and 46 ml of 48% hydrogen bromide was heated at 100°–105° C. for 3 hours and then left at room temperature overnight. 400 ml of anhydrous ethyl ether was added to the mixture to form a second mixture which was then refrigerated 3 days. The second mixture was then filtered to produce a yellow crystalline residue. The residue was washed with anhydrous ethyl ether and air dried.

EXAMPLE 2

Preparation of 2',6'-Dimethyl-4'-(sulfomethylcarbamoyl) phenyl 10-methyl-acridinium-9-carboxylate bromide (DMAE-AMS)

A solution of 2',6'-dimethyl-4'-carboxylphenyl 10-methyl-acridinium-9-carboxylate bromide (DMAE-COOH, 20 mg, 0.043 mmole) in 2 ml of dimethylformamide (DMF)/$CHCl_3$ (1:1) was cooled in an ice bath, treated with triethylamine (31 ul, 0.215 mmole) and ethyl chloroformate (6.1 ul, 0.065 mmole) to form a reaction mixture. After 30 min. the reaction mixture was evaporated. The residue of the evaporation was reconstituted in 2 ml of DMF, treated with triethylamine (31 ul, 0.215 mmole) and aminomethanesulfonic acid (9.5 mg, 0.086 mmole) to form a second reaction mixture. The second reaction mixture was stirred at room temperature overnight, and evaporated. The crude product so formed was purified on one analytical TLC plate (Silica gel 60, F254, Merck & Co., Inc., Rahway, N.J.), and developed with chloroform/methanol/water (65:25:4). The yellow band which developed on the plate (Rf=0.38) (which could also be detected under both long and short UV light) was stripped from the plate and eluted with the same solvent system. The eluent so produced was evaporated and the residue of the evaporation triturated with methanol to form a mixture. This mixture was then filtered through a polycarbonate membrane (13 mm diameter, 0.2 um pore size) (Nucleopore Corp., Pleasanton, Calif.) mounted on a syringe filter holder, and the filtrate so produced was evaporated to give DMAE-AMS (15 mg, 62%).

EXAMPLE 3

Preparation of 2',6'-Dimethyl-4'-[N-7-(1,3-disulfonaphthalenyl)carbamoyl]phenyl 10-methyl-acridinium-9-carboxylate Bromide (DMAE-ANDS)

A solution of 2',6'-dimethyl-4'-carboxylphenyl 10-methyl-acridinium-9-carboxylate bromide (DMAE-COOH, 18 mg, 0.038 mmole) in 3.6 ml of a dioxane/water (1:1) mixture was treated with 1-(3-dimethylaminopropyl)-3-ethylcarbodiimide hydrochloride (37 mg, 0.193 mmole, Aldrich Chemical Co., Inc., Milwaukee, Win.) at room temperature for 5 minutes to form a reaction mixture. A solution of 7-amino-1,3-naphthalenedisulfonic acid (ANDS, 26 mg, 0.076 mmole, Aldrich Chemical Co., Inc.) in 0.9 ml of water was added to the reaction mixture which was then stirred at room temperature overnight and evaporated.

The residue of the evaporation was dissolved in a minimal amount of 0.1M sodium carbonate to obtain a solution at neutral pH. This solution was mixed with an equal amount of methanol and purified on a 20×20cm preparative TLC plate (Silica gel 60, F254, Merck & Co., Inc.), and devel-